United States Patent
Bergersen

(10) Patent No.: US 12,075,983 B1
(45) Date of Patent: Sep. 3, 2024

(54) METHODS AND DEVICES FOR PHOTOGRAPHING UPPER AND LOWER DENTITIONS

(71) Applicant: ORTHO-TAIN, INC., Toa Alta, PR (US)

(72) Inventor: Earl O. Bergersen, Glenview, IL (US)

(73) Assignee: Ortho-Tain, Inc., Toa Alta, PR (US)

( * ) Notice: Subject to any disclaimer, the term of this patent is extended or adjusted under 35 U.S.C. 154(b) by 0 days.

(21) Appl. No.: 18/447,844

(22) Filed: Aug. 10, 2023

(51) Int. Cl.
| | |
|---|---|
| A61B 1/247 | (2006.01) |
| A61B 90/00 | (2016.01) |
| A61C 9/00 | (2006.01) |
| A61C 19/05 | (2006.01) |

(52) U.S. Cl.
CPC .............. *A61B 1/247* (2013.01); *A61B 90/06* (2016.02); *A61C 9/0053* (2013.01); *A61C 19/05* (2013.01); *A61B 2090/061* (2016.02)

(58) Field of Classification Search
None
See application file for complete search history.

(56) References Cited

U.S. PATENT DOCUMENTS

| | | | | |
|---|---|---|---|---|
| 2008/0124677 A1* | 5/2008 | Ertl | ...................... | A61C 9/0053 433/196 |
| 2011/0195373 A1* | 8/2011 | Waugh | ..................... | A61C 7/02 433/24 |
| 2012/0088205 A1* | 4/2012 | Dragan | .................... | A61C 5/90 433/31 |
| 2014/0170590 A1* | 6/2014 | Whalen | ................. | A61B 1/247 433/30 |
| 2018/0228359 A1* | 8/2018 | Meyer | ...................... | G06T 7/70 |

* cited by examiner

*Primary Examiner* — Rebecca A Volentine
(74) *Attorney, Agent, or Firm* — Taft Stettinius & Hollister LLP

(57) ABSTRACT

A photo enhancer device is provided that includes a mirrored plate and a transparent plate connected with a stiff, resistant, or resilient living hinge that opens up the plates automatically with force when located within an open mouth. The disclosed method and appliance determines sizes and positions of dentition of arches, and more particularly relates to photographing dentition and arches using a mirrored plate.

25 Claims, 4 Drawing Sheets

METHODS AND DEVICES FOR PHOTOGRAPHING UPPER AND LOWER DENTITIONS

TECHNICAL FIELD

The present disclosure relates to a method and appliance determining sizes and positions of dentition of arches, and more particularly relates to photographing dentition and arches using a mirrored plate.

BACKGROUND OF THE DISCLOSURE

The statements in this section merely provide background information related to the present disclosure and should not be construed as constituting prior art.

In in order to aid in the diagnosis of a patient's orthodontic condition, photographs are commonly used for an initial diagnosis, as well as for follow-up progress checks every few months. The recorded images are permanently stored for the patient. Images or records of the dentition can be obtained in several different ways. Simple angulated photos can be used; however, any measures of the dentition are inaccurate due to the camera angle needed for the photograph. Photos or photocopies of models can be used, or digital images of the actual dentition is another recent method available.

In recent years an optical scan of the patient's dentition can be made using a powered wand that produces a digital scan of the dentition in a 1 to 1 format.

All of these various techniques involve an office visit with an office assistant or dentist to take such records. While these techniques provide a relatively accurate record of a patient's dentition, the amount of time and expense required to obtain such records can be time consuming and cost prohibitive.

What is needed, therefore, is a photographic device or process to obtaining a patient's record that reduces the amount of time needed to obtain the record and reduces the cost of obtaining such records.

SUMMARY OF THE DISCLOSURE

The present invention relates to a method and device of obtaining a photograph of the occlusal and incisal dentition of a patient with the use of a clear plate that overlays the upper and lower dentition. In different embodiments, the plate is made of plastic or glass. As described herein, the plate is referred to as plastic but other clear materials that transmit light are contemplated. This clear plate is hinged to a mirror, such as a mirrored plate that reflects an image of the lower and upper dentitions of a patient depending on the orientation of the device. In one embodiment, a hinge, is made from a polypropylene living hinge and connects the mirrored plate to the transparent plate. The living hinge makes it easier to place the device in the mouth of a patient without two different separate plates that are required to be held in the mouth at the same time. The living hinge remains in an open position until compressed or closed by the patient.

A photo is taken of the reflected image displayed in the mirrored plate. The reflected image is obtained from a number of different types of cameras, including but not limited to a cellular phone having a camera, a tablet device or phone having a camera, or a camera, including both film and digital cameras. The photograph of the reflected image is used to measure features of dentition, including but not limited to crowding and spacing of the dentition, arch widths, inclinations of teeth, displacements and abnormal positions of teeth, sizes of teeth, available and required spaces of dentition. These features are used to determine sizes of appliances, including but not limited to dentures, retainers, mouth guards, and the severity of over jet can be measured from the image produced by the camera.

The transparent plate includes, in one embodiment, indicia printed on its surface or embedded at or within the transparent plate, to enable the calculation the teeth dimensions, such as the width or sizes of the teeth. In one embodiment, two squares, each including sides of 5 mm, enables the user to obtain a 1:1 calculation of size of the dentition. In one or more embodiments, the plate includes a QR code image. The QR code image, in different embodiments, includes a square or a rectangular shape. Other shapes are contemplated. To identify dentitions sizes based on photographs of different patients, the QR code includes a uniform QR code that is printed on the transparent plate at a location that does not obstruct important details of the teeth, mouth, or jaw. QR codes of the same size would be used for all patients to determine the actual sizes of the dentition etc.

In one embodiment, a single photo provides sufficient information to the user to determine the need for a certain type of appliance. In other embodiment, a series of photos taken over time of a patient's dentition provide information as to the progress of treatment, amount of improvement, and cooperation from positive changes, if present, in crowding, rotations and space closure etc.

With the procedure as described herein, the clear transparent plate is adapted to be centered on the upper or lower dentition and the hinged mirror opens inside the mouth to expose the reflected image underneath the transparent plate. Once opened and properly located, the camera, i.e., a cell phone, tablet device with a camera, or a digital or analog camera, is used to take a photo which can be taken by a layperson, such as parent, or by the practitioner, or an assistant to the practitioner. Both the parent and the patient can be located remotely from a practitioner's office, thereby reducing or eliminating the need for an office visit. The photographic images, in one embodiment, are emailed to a diagnostic center or to a dentist's office for an analysis of the condition without an office visit. In another embodiment, the photographic images are transferred by a cell phone application to the cloud and stored in a remote server, which can be accessed through the web. In one alternative, the photographic procedure is to have a photo taken in the dental office by a dental assistant or by the dental professional. In any event, the photographer, whether the layperson, the dental assistant, or dental professional are not required to have extensive training when taking the photos.

In another embodiment, a cleat or extended stop can be molded into the reverse side of the mirrored plate facing the dentition to create a stop for the mirrored plate when the hinged device is in a closed position to be positioned against the labial of the lower central incisor. Once located, a photo of the upper front tooth or teeth, is used to make a horizontal measurement of the transparent plate with printed amounts on it to determine the severity of an over jet. The photograph provides an accurate horizontal location of the upper central incisor in relation to the lower incisor which is then measured from the photo to give the over jet measurement.

In one embodiment, the hinge that connects the transparent and mirrored plates is molded from a polypropylene or another or similar plastic in order to make the hinge strong enough to keep the mirrored and transparent plates open in an automatic fashion. The hinge function makes the device to open as wide as the patient can open their mouth automatically.

In a further embodiment, extended laterally located handles extend from the front end of the device and sticks out of the mouth, so that the transparent plate can be held in position against the teeth if needed (not illustrated).

In a further embodiment, there are handles extending from the front end that extend from the mouth of the patient at either side of a midline of the device for additional support of the photo enhancer in order to be well centered and positioned within the patient's mouth. These handles are inclined with respect to the midline and enable a practitioner to use both hands to move the device from side to side for proper positioning. In one embodiment (not shown), the centrally located handle, if included, is centrally located at the midline. These handles extend from both the mirrored and transparent plates of the photo enhancer device.

Using these handles, the patient holds the transparent plate down against the lower (or upper) teeth with these handles, if needed so as to minimize errors in when taking a photo of the lower (or upper) dentition. The patient, in addition, also holds the transparent plate up against the upper teeth with these handles, if needed, again to minimize errors in the photo taken of the upper dentition. When taking photos of the upper teeth, the photo enhancer is reversed, i.e. rotated about 180 degrees, so that the transparent plate is held against the upper teeth while the mirrored plate is separated from the transparent plate and located at the lower dentition so a photograph can be taken of the upper dentition in a similar way that the lower dentition is taken.

The mirrored plate, in one embodiment, is mounted to a plastic backing plate or substrate that includes a rim surrounding an inserted mirror to prevent the mirror's dislodgement from the photo enhancer device.

The entire photo enhancer device in one embodiment (before the mirror is attached) is molded as a one-piece unitary part from a polypropylene plastic, which is at least partially transparent. The one-piece unitary part is made to include two relatively rigid parts connected by a living hinge. Placement of the mirror on one of the parts covers up a first portion of the unitary part, and certain printing, i.e. indicia, is located on the remaining unitary part. In other embodiments, the two separate parts are formed individually and connected by a hinged portion, such as a living hinge. Other types of hinges are contemplated. In some embodiments, the mirror is made of highly polished steel that is magnetized so that it is held in place in a molding die magnetically, so it will not slip out of place during the molding process of the one-piece unitary part around the mirrored plate. A QR code in different embodiments is included with the indicia.

The small printed squares or QR codes are located along a midline of the transparent plate where a first printed square is located toward a front portion of the transparent plate and a second printed square is located toward a middle or rear portion of the transparent plate depending on the size of the device. In one embodiment, each of the squares is printed in a 5×5 mm format, the purpose of which is to accurately determine the sizes of the dentition which is in direct contact with this transparent plate. In other embodiments, other sizes and shapes of measurement indicia are contemplated, and such measurement indicia includes one or more markings. The measurement indicia enables a diagnosis of an orthodontic problem. In one embodiment, the squares are black in color and include sharp edges and corners to provide an accurate identification of measurements. Other embodiments are contemplated including measurement indicia having shapes with sides indicated by lines, but where the interior of the shapes is transparent. In one or more embodiments, indicia includes the QR code for a computer to identify the enlargement or reduction of the photo of the dentition to determine actual sizes of the dentition.

A printed line, which also may be embedded, is located on the transparent plate to indicate a position of a stop molded into the back of the mirrored plate. The stop extends from the back of the mirrored plate and acts to block movement of the device once located. The stop is positioned against the labial margin of the lower central incisor or incisors when the photo enhancer is in a closed position against the lower dentition.

The above printed line indicates the position of the lower incisal dentition, and several measurement indicators, printed on the transparent plate are located in front of this line, i.e. toward the patient's upper incisors. The measurement indicators indicate the position of the upper central incisor in relation to the position of the central incisors of the lower dentition. The measurement of the position of the upper central incisor in relation to the lower central incisor indicates the severity of over jet. A simple photo of the mirror placed against the lower dentition indicates the position of the upper incisor in relation to the measurement indicators. The resulting photo is then utilized for the measurement of the over jet.

The sizes of the 5×5 mm squares or other dimensions printed on the transparent plate are used to obtain a relatively exact width and sizes of the teeth of the actual patient's dentition seen below this transparent plate. The exact measures of the sizes of these teeth (upper and lower) are used to determine the various measures necessary for an accurate diagnosis of the patient's occlusion. From this photo, a calculation is made to determine the actual sizes of the patient's teeth and dentition. Using the calculated information, the following items are determinable if desired: 1) available and required spaces around the lower and upper arches; 2) the sizes of appliances if required; 3) arch widths; 4) crowding or spacing present; 5) over jet; 6) space is required for proper movement of displaced anterior and posterior teeth (particularly premolars, molars and canines); 7) rotations and displacements of teeth; 8) broken contacts, i.e. where teeth are rotated so they do not contact each other in a straight or sequential manner, and other measurements of the dentition that may be needed for a proper diagnosis. Once arch width is measured with this photo of the dentition, the measured arch is compared, if needed, to statistical data on such widths to determine if treatment is required or not. The printed squares are used to be able to determine the amount of shrinkage or enlargement in the photos and by using the proportion of change one can determine the size of the teeth and dentition to an accurate amount. The printed squares are used by a computing device and computer program software to estimate an enlargement or shrinkage of the photographic image of the dentition so the computer can properly estimate the 1:1 size of the one or more measures that the computer device makes (over jet, available space, required space, posterior arch width, the width of various teeth which are needed to estimate the proper size of the appliance). This estimate size can be transferred to any other photo of the dentition or patient in order to measure other dimensions, for example overbite, gummy smiles etc.

When one subtracts the required space from the available space, the difference, is indicated by a one or more numbers on either side of a horizontal line between a value of −2 and a range of values of 2-14 are used to determine an amount of crowding. The numbers 2-14 are used by the computer program software to make an overjet measurement or by an individual visually reviewing an amount of overjet without the use of computer analysis. Also, an individual in some circumstances makes a visual review to check the accuracy of the computer measurement.

Under some circumstances, double images of the printed data that is located on the transparent plate is reflected from the mirrored plate as a result of the two plates being closed together but not completely. To prevent the double images from occurring, a white overlying sheet or plate is placed between the mirror and the transparent sheet. Not only does this prevent double images from occurring, the white sheet or plate improves the imaging of the overjet being measured due to the contrast between the white sheet and the black measurement indicia. In one embodiment, the white sheet or plate is held in place magnetically to cover the portion of the mirrored plate that reflects the printed material from the transparent plate when the photo is being taken. In some embodiments, the white sheet includes a magnetized portion that is attracted to a metalized highly polished mirror surface. In another embodiment, the mirror is located on a backing support that is magnetized to receive a white sheet or plate of metal that is magnetically attracted to the magnetized backing support.

In another embodiment, there are handles extending from the front section of the transparent plate so that the patient can secure this plate directly against the anterior and posterior teeth of the arch that is being photographed. In one embodiment, there may be a centrally located handle and two shorter side handles extending from the front of both the transparent and mirrored plates of the photo enhancer device. The middle handle is longer so the patient's fingers don't interfere with the holder of the camera, cellular phone or tablet device when taking the photographs.

The location of the stop, molded into the outside of the mirrored plate, is identified with a marking, such as a horizontal marking with respect to the midline, located on the mirrored plate. When the stop is positioned against the lower central incisors, the horizontal marking or line on the mirrored plate indicates the exact position of the lower incisors.

Measured markings on the same transparent plate proceed forward and rearward toward the upper incisors from this horizontal line, with respect to a longitudinal axis of the device to indicate the position of the upper incisors with respect to the transparent plate located over the lower dentition. These measures indicate approximately, in spaced markings, the distance forward from this horizontal line determining the upper incisal edges and their labial or lingual extent of these incisors in a forward or rearward direction from the lower incisors. The spaced marking provide incremental measurements, such as in inches or millimeters. When the photo enhancer device is closed together so that the mirrored and transparent plates are facing each other, the device is placed into the mouth with the exterior of the mirrored surface placed against the occlusal surface of the lower teeth. The device is pushed in a rearward direction, toward a patient's throat, until the stop engages the labial surface of the lower central incisors. The patient then is asked to close their mouth down and a photograph is taken of the transparent plate with measured markings to determine the position of the upper central incisors and their relative distance from the lower incisors is in either a forward (overjet) or rearward (Class III) position. The resulting upper incisor photo is then measured from the photograph in order to determine the exact over jet or Class III (rearward or forward position of the lower jaw) of the patient according to the upper incisors position in relation to the small horizontal lines.

In one embodiment, there is provided a photo enhancer device for imaging dentition of an individual including a transparent plate and a mirrored plate connected to the transparent plate with a living hinge to form a one piece unitary part. The transparent plate and the mirrored plate are sized to fit, at least partially, in the mouth of a patient for imaging the individual's dentition.

In some embodiments, the photo enhancer device includes wherein the transparent plate and the mirrored plate are sized to provide occlusal images of the lower and upper arches.

In some embodiments, the photo enhancer device includes wherein the living hinge includes a stiff and strong living hinge having a sufficient resiliency to maintain the living hinge in an open position in the absence of an externally applied pressure.

In some embodiments, the photo enhancer device includes wherein the transparent plate includes measurement indicia to provide one or more of the following: 1) size determination of the upper and lower teeth, 2) available spaces between teeth; 3) required spaces between teeth; 4) crowding and spacing of teeth; 5) broken contacts; 6) sizes of various dental appliances, 7) arch widths; 8) severity of an overjet; 9) Class III (lower jaw over growth); 10) and other measurements required for a diagnosis of an orthodontic problem.

In some embodiments, the photo enhancer device includes wherein the mirrored plate includes a mirror located on one side of the plate and a stop extending from another side of the plate, wherein the stop is adapted to engage a lower incisor to measure an overjet or Class III with an upper central incisor.

In some embodiments, the photo enhancer device further includes measurement indicia located at the transparent plate, wherein the measurement indicia provides dimensional information for the upper and lower arches.

In some embodiments, the photo enhancer device includes wherein the measurement indicia includes a first two-dimensional indicator spaced from a second two-dimensional indicator, wherein each of the first and second two-dimensional indicators have first and second sides of a known length, wherein a photograph of the dentition and of the first and second two-dimensional indicators enables determining sizes of the photographed dentition.

In some embodiments, the photo enhancer device includes wherein the transparent plate includes a centerline along which the first and second two-dimensional indicators are located.

In some embodiments, the photo enhancer device includes wherein the measurement indicia includes a measurement scale located along the centerline between the first and second two-dimensional indicators to determine distances and sizes of the photographed dentition.

In some embodiments, the photo enhancer device of includes wherein the measurement indicia includes a stop line, wherein the stop line indicates a position of the stop when the mirrored plate and the transparent plate are in a closed position.

In some embodiments, the photo enhancer device includes wherein the mirrored plate or the transparent plate includes one or more handles to enable the mirrored plate or the transparent plate to be held in contact with the dentition of either the lower arch or the upper arch.

In some embodiments, the photo enhancer device includes a white plate that inserts over the mirrored plate and is held in place by magnetism to substantially prevent a double image of measurement indicia located on the transparent plate when the mirrored plate and transparent plate are held together in order to measure over jet.

In another embodiment, there is provided a measuring tool located at a transparent plate of a photo enhancer device used to diagnose an orthodontic problem of a patient. The measurement tool includes measurement indicia printed on or embedded at or within a surface of the transparent plate in order to determine sizes of upper and lower teeth, available and required spaces, crowding and spacing, broken contacts, sizes of various appliances, arch widths, and severity of the overjet or Class III conditions with a stop against the lower incisors with measures to the upper central incisors, and other measures needed for a diagnosis of an orthodontic problem.

In some embodiments, the measuring tool includes wherein the measurement indicia includes a first two-dimensional indicator spaced from a second two-dimensional indicator, wherein each of the first and second two-dimensional indicators have first and second sides of a known length with or without QR codes, wherein a photograph of the dentition and of the first and second two-dimensional indicators enables determining sizes of the photographed dentition.

In some embodiments, the measuring tool includes wherein the transparent plate includes a centerline along which the first and second two-dimensional indicators are located.

In some embodiments, the measuring tool includes wherein the measurement indicia includes a measurement scale located along the centerline between the first and second two-dimensional indicators to determine distances of the photographed dentition.

In some embodiments, the measuring tool includes wherein the measurement indicia includes a stop line, wherein the stop line indicates a position of the transparent plate with respect to a lower incisor of the patient.

In a further embodiment, there is provided a photo enhancer device having a mirrored plate and a transparent plate used to diagnose an orthodontic problem of a patient. The photo enhancer device includes a living hinge connecting the mirrored plate with the transparent plate, wherein the living hinge opens forcibly automatically as the patient opens their mouth and substantially prevents the patient from breathing directly on the mirror which eliminates a problem of clouding up the mirror which interferes with the clarity of photographs utilizing the photo enhancer device.

In another embodiment, the mirrored plate can be heated to prevent clouding of its surface when the patient breathes.

In some embodiments, the photo enhancer device includes wherein the living hinge includes a strong and stiff living hinge fixedly connected to the mirrored plate and the transparent plate to provide a unitary photo enhancer device.

In some embodiments, the photo enhancer device includes wherein the living hinge includes polypropylene or other plastic having a sufficient resiliency to open by itself in the absence of an externally applied pressure.

In an additional embodiment, there is provided a set of orthodontic tools used to diagnose an orthodontic problem of one or more patients. The set includes a first photo enhancer device having a first transparent plate connected to a first mirrored plate with a first living hinge, wherein the first photo enhancer device includes a first size. The set also includes a second photo enhancer device having a second transparent plate connected to a second mirrored plate with a second living hinge, wherein the second photo enhancer device includes a second size. The first size and second size are different sizes adapted to accommodate different sizes of oral cavities of one or more patients.

In some embodiments, the set of orthodontic tools includes wherein the different sizes are adapted to accommodate different sizes of teeth and the number of teeth present at various ages from an infant through adulthood of the one or more patients.

In a still further embodiment, there is provided a method of imaging dentition of an individual including: providing a photo enhancer device used to diagnose an orthodontic problem of a patient, the photo enhancer device having a mirrored plate and a transparent plate connected with a living hinge; imaging, at a first time, the dentition of the individual using the photo enhancer device to arrive at an initial diagnosis of the individual; imaging, at a second time, the dentition of the individual using the photo enhancer device to arrive at a follow-up diagnosis of the individual to determine a progress of treatment for a malocclusion.

In some embodiments, the method includes imaging, at one or more times after the second time, the dentition of the individual using the photo enhancer device to arrive at additional follow-up diagnoses of the individual to determine the progress of treatment for the malocclusion.

In some embodiments, the photo enhancer device further includes a QR code.

ADVANTAGES

In one embodiment, the device is a one-piece mirrored photo enhancer device to enable a relatively direct photo of the dentition. In contrast, photos that are taken directly of the dentition in an open mouth position will duplicate the dentition from an angle. The resulting photo is not conducive for providing accurate measures of: 1) sizes of teeth and 2) distances within the upper or lower dentitions.

Since the one-piece photo enhancer device is designed as a one piece insert with the flexible hinge, the plates of the device extend from and open with respect to the hinge within the mouth. The flex point of the hinge improves the ease with which the device is held in the mouth, thereby eliminating the need for a third person to hold a separate two-piece mirrored device inside the mouth.

Since this device is hinged in the rear section, the mirrored plate is separated from and blocks hot moist air exiting from the throat when the patient breathes. As a result, the mirror does not become clouded up, which would otherwise interfere with accurate photo taking.

One can determine the actual size of the teeth and dentition from the printed squares on the transparent plate that are in close contact with the dentition, since the transparent plate is being held directly against the occlusal surfaces of either the upper or lower dentition. To insure the positioning and stability of the device when photos are taken, one or both of the handles that extend from the front of the device are held by the patient. Also, since these handles are inclined with the centerline of the device, a patient's hands do not block the taking of the photos.

One can measure both the available and required spaces more accurately than if the photo is taken without a mirror, since in such a case, the camera needs to be positioned at an angle with respect to the dentition, which seriously distorts measurements.

One can determine the required space of the dentition more accurately, since the actual sizes of the teeth can be determined through compensation due to enlargement or shrinkage using the small squares (5×5 mm.) and comparing them to the measures of the widths of one or more of the permanent incisors in the lower arch.

One can also more accurately determine the amount of crowding of the patient's dentition. By subtracting the required space from the available space, and if the required space is more severe than the available space indicated by a (-), the amount of crowding is accurately determined.

One can then determine and select more accurately the sizes of appliances required for the correction of the malocclusion, i.e. misaligned teeth leading to oral health complications. The selection of appliances is based from one or both of the available space and the required space usually of the lower arch. The required space indicates the size of a final appliance that would be used by the patient, and if the difference between the available space and the required space exceeds 3 mm, two separate appliances would be used, the first being three half sizes (or 2.4 mm.) larger than the available space, and the second would be determined by the sizes of the teeth indicated by the required space.

One can also determine more accurately the arch width of the dentition as opposed to taking an angular photograph of either the upper or lower dentition without the use of a mirror.

The photo enhancer device including the mirror is manufactured quite inexpensively, so that they can be issued to doctors, parents or patients at a low cost. As a result, the photo enhancer device could be issued to every parent of patients so that they can take future photographs to indicate the progress of treatment of their child or patient without ever visiting the office. These progress photos are then simply emailed to the office and a doctor or whoever is following the case can then inform the patient whether sufficient wear or progress is being made in their case remotely from the office and suggest changes if required.

A relatively stiff living hinge connecting the mirror and transparent plates into one single unitary device is made of a stiff, flexible, and strong material sufficient enough so that the two plates are forcibly held open and do not have to be held open by the patient when placed into the mouth. In this way, the hinge provides an important advantage that enables the patient to hold the transparent plate against either the lower or upper dentition which ever arch is having a photo that is being taken. The force of the hinge opening and closing of the mirror and the transparent plate in order to measure dentition, including overjet, ranges from substantially 2 ounces to substantially 2 pounds of force regardless of the sizes of the devices for different ages of patients.

The photo enhancer is used to aid in picture takings of both the upper or lower arches.

The hinged plates of the photo enhancer help maintain an open position due to the stiff living hinge and does not require a third person to hold the mirror in the patient's mouth, which is required when a hinge is not present.

The hinged plates are maintained in an open position without the help of a person who would be required to hold the plates in an open position for a proper photo.

The only responsibility of the patient is to hold the transparent plate directly against the entire dentition whether it be the upper or lower whichever is being taken.

The photo enhancer device is made in one or more different sizes to be used by children and adults due to the various sizes of their oral cavities and the addition of further teeth from five years through adulthood, or even at younger ages than five if required.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE DRAWINGS

The above-mentioned aspects of the present application and the manner of obtaining them will become more apparent and the teachings of the present application itself will be better understood by reference to the following description of the embodiments of the present application taken in conjunction with the accompanying drawings, wherein.

DETAILED DESCRIPTION

Figure 1:
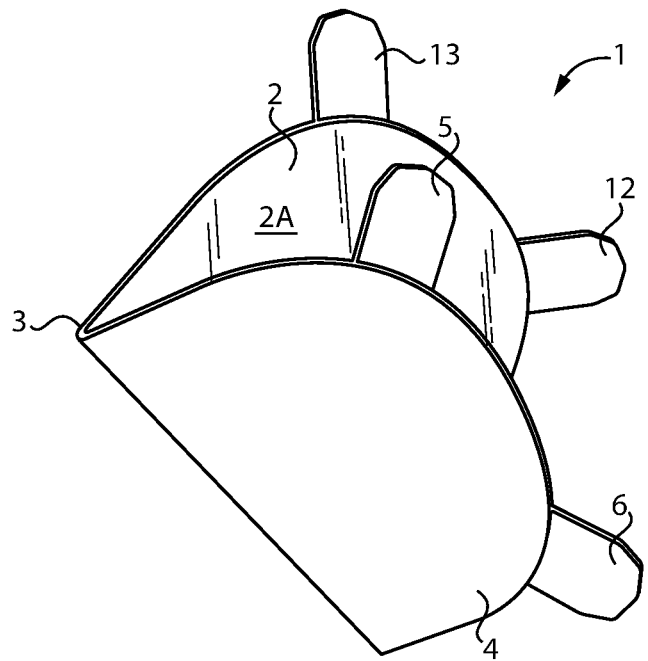
FIG. 1 illustrates a perspective side view of an intraoral hinged mirrored photo device to enable direct head on photos of an individual's dentition with minimal distortion.

Throughout this disclosure, various quantities, such as amounts, sizes, dimensions, proportions and the like, are presented in a range format. It should be understood that the description of a quantity in range format is merely for convenience and brevity and should not be construed as an inflexible limitation on the scope of any embodiment. Accordingly, the description of a range should be considered to have specifically disclosed all the possible sub-ranges as well as all individual numerical values within that range unless the context clearly dictates otherwise.

For example, a description of a range such as from 1 to 6 should be considered to have specifically disclosed sub ranges as from 1 to 3, from 1 to 4, from 1 to 5, from 2 to 4, from 2 to 6 etc., 1.1, 2, 2.3, 4, 5, and 5.9 etc. This applies regardless of the breadth of the range. The upper and lower limits of these intervening ranges may independently be included in the smaller ranges, and are also encompassed within the disclosure, subject to any specifically it excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a", "an", and "the" are intended to include the plural forms as well, unless the context clearly indicates otherwise. It will be further understood that the terms "includes", "comprises", "including" and/or "comprising", when used in this application, specify the presence of stated features, integrators, steps, operations, elements, and/or components, but do not preclude the presence or addition of one or more other features, integrators, steps, operations, elements, components, and/or groups thereof. As used herein, the term "and/or includes any and all combinations of one or more of the associated listed items. Additionally, it should be appreciated that items included in a list in the form of "at least one of A, B and C" can mean (A); (B); (C); (A and B); (B and C); (A and C); or (A, B, and C). Similarly, items listed in the form of "at least one of A, B, or C" can mean (A), (B), or (C); (A and B); (B and C); (A and C) or) A<B and C).

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The embodiments of the present disclosure described below are not intended to be exhaustive or to limit the disclosure to the precise forms and the following detailed description. Rather, the embodiments are chosen and described in an exemplary manner so that others skilled in the art may appreciate and understand the principles and practices of the present disclosure. Further, this application is intended to cover such departures from the present disclosure as come within known or customary practice in the art to which this invention pertains.

FIG. 1 illustrates a perspective side view of an intraoral hinged mirrored photo device (1) to enable direct head on photos of an individual's dentition with minimal distortion. The device 1 includes a mirrored plate (2) which is connected with a hinge (3), preferably a living hinge, which is connected to a second plate (4), i.e. a transparent plate. The second plate (4) due to its transparency, reveals the dentition where the plate (4) is placed. The dentation seen through the transparent plate (4) is reflected by the mirrored plate (2) at a mirrored surface (2A), to enable photos to be taken of the dentition that appears on the mirrored plate (2). While the living hinge (3) is shown having the same thickness as the mirrored plate (2) and the transparent plate (4), in other embodiments, the thickness of the living hinge (3) is different than either the thickness of the mirrored plate (2) or the transparent plate (4). In one embodiment, for instance, the thickness of the living hinge (3) is greater than the plates to which it is connected.

When the device (1) is placed into the mouth and the lower dentition is being photographed, the transparent plate (4) is held against the lower dentition so that this transparent plate (4) is in direct contact with the entire lower dentition. The transparent plate (4) includes handles (5) and (6) that are inclined with respect to a centerline (7) that extends longitudinally along the device (1) and through the hinge (3). The transparent plate (4) is held down against the lower dentition by the patient applying downward pressure to one or both of the laterally extending handles (5 and 6) or by the longer optional middle (not shown) located in the middle of the lower transparent plate (4) extending in the direction of the centerline 7. In some embodiments, the centerline (7) is marked on the transparent plate (4), but in other embodiments, it is not marked.

A similar procedure is used for photographing the upper arch of the patient when the transparent plate (4) is held in a similar way to the upper dentition by either the lateral handles (5 and/or 6) or by the longer optional middle handle (not shown).

The mirrored plate (2), when taking a photograph of the lower or upper arch, is maintained in an open position in the mouth when the individual has sufficiently opened the mouth. The living hinge (3), in one embodiment, includes a sufficient stiffness, i.e. resiliency, to force the plate (2) and plate (4) apart such respective ends (2B) and (4A) are spaced apart when the mouth is located in the open position. Consequently, the plates (2) and (4) are automatically opened and maintained in the open position without the help of the patient. In one embodiment, the mirrored plate 2 includes handles (12) and (13) to hold the mirrored plate 2 against the dentition not being photographed. The individual may also press the handles 12 and 13 against the detention not being photographed while having the mouth in the open position such the transparent plate 4 is pressed against the dentition being photographed. The person taking the photo with the camera can then focus the camera against the mirrored plate 2 to take a photo of either the lower or upper dentition, depending on the location of the transparent plate. Generally, the transparent plate (4) is held directly against the upper or lower dentition by the patient using the various handles (5,6) or holding the mirrored plate (4) against the upper or lower dentition not being photographed by the handles (12) and (13), whichever is most convenient without interfering with the person taking the photograph. In other embodiments, the device (1) includes only one set of handles (5) and (6) or (12) and (13). Also, in further embodiments, the living hinge (3) includes an embedded wire hinge that extends across a hinge centerline (3A) to provide an additional amount of resiliency to the living hinge (3) if desired.

Figure 2:
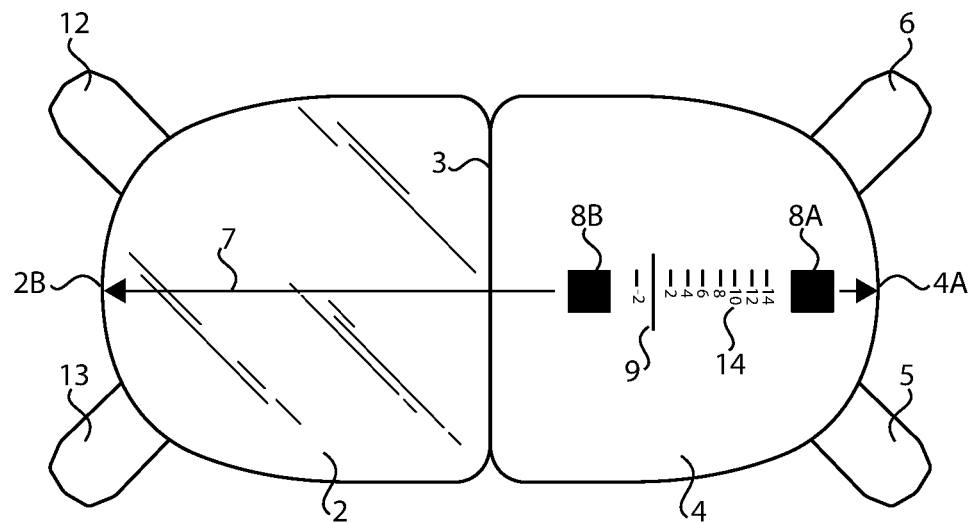
FIG. 2 illustrates a plan view of a photo enhancer device in an opened position.

The transparent plate (4) has first and second two dimensional indicators (8A and 8B) which are located on the transparent plate (4) as seen in FIG. 2 which may include a QR code within its interior (not shown). Indicator 8A is located anteriorly and indicator 8B is located posteriorly. In one embodiment, the two dimensional indicates are squares (8A and 8B) that are applied to one or both of the surfaces of the transparent plate (4) by a printing process. In other embodiments, the two dimensional indicators (8A and 8B) are formed within the transparent plate (4) during manufacture of the plate (4). The two dimensional indicators (8A and 8B) are formed with a known width and a known length to determine tooth sizes and spacing between teeth. A first two-dimensional indicator is spaced from a second two-dimensional indicator, wherein each of the first and second two-dimensional indicator have first and second sides of a known length. A photograph of the dentition and of the first and second two-dimensional indicators enables determining sizes of the photographed dentition. The computer, having determined tooth sizes, has the ability to determine both tooth sizes and measured dimensions from any other photo images taken by other techniques as well.

In a further embodiment, the squares (8A and 8B) include sides of 5 mm such that the square is 5×5 mm square. Other dimensions are contemplated including rectangular dimensions. In any configuration, the known dimensions are used to determine a reduction or an enlargement of the image resulting from the photograph taken via the mirrored plate (2) that includes images of the two dimensional indicators (8A and 8B). In different embodiments, the indicators (8A and 8B) are the same sizes or are different sizes having predetermined and known dimensions.

Figure 4:
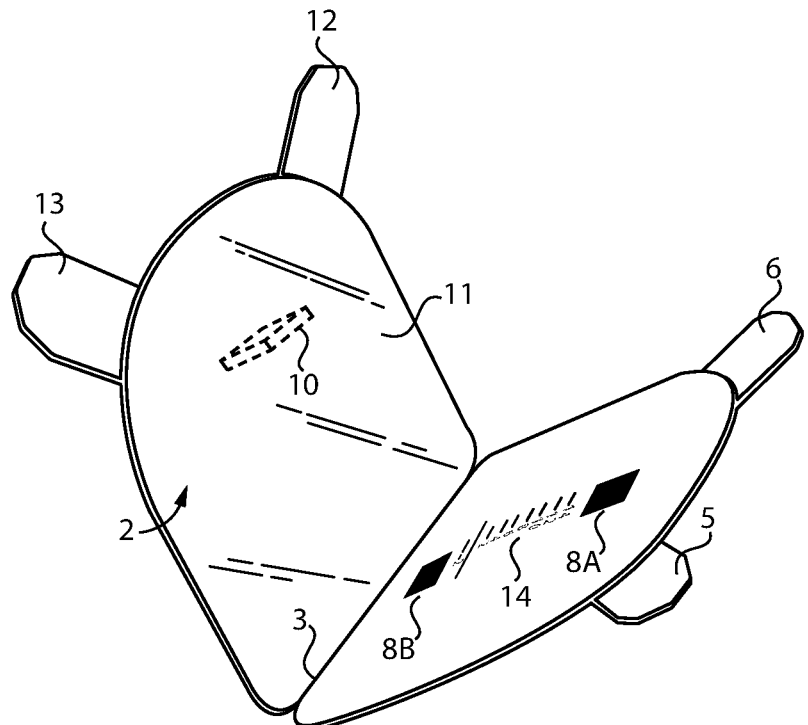
FIG. 4 illustrates a perspective side view of the outside of an intraoral hinged photo enhancer device.
Figure 5:
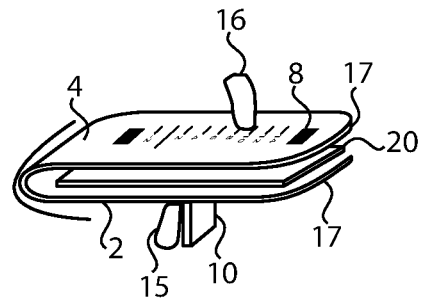
FIG. 5 illustrates a side plan view of one plate of a photo enhancer device.
Figure 7:
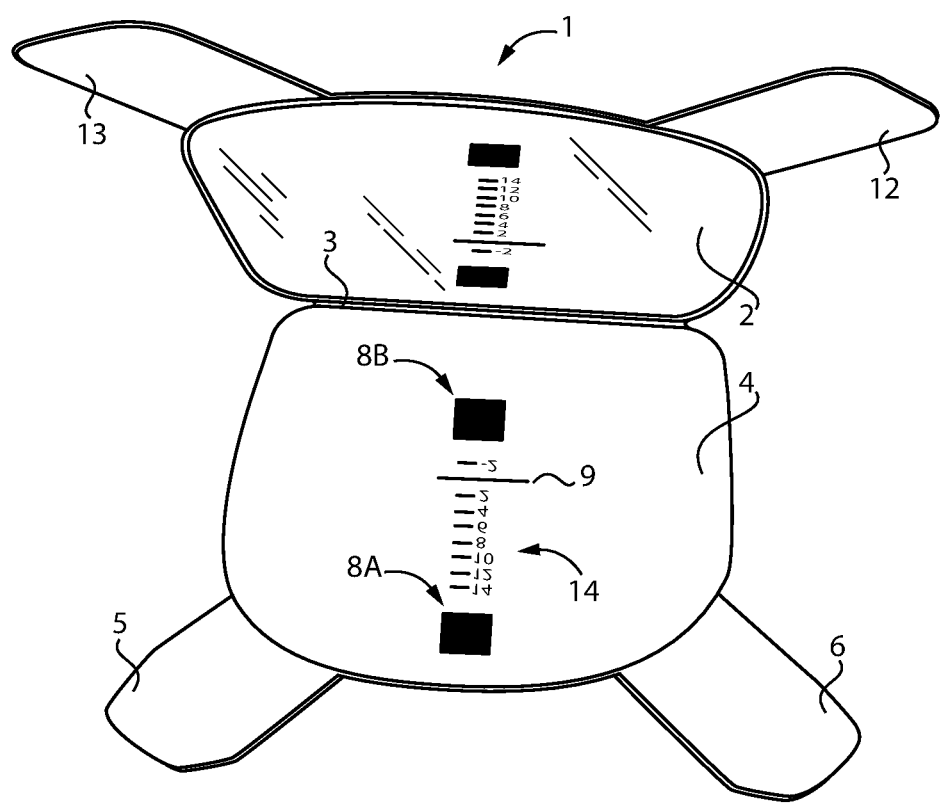
FIG. 7 illustrates a front view of an intraoral hinged mirrored photo device including a transparent plate having measurement indicia.

A linear scale (14), including a plurality of numbers of FIG. 4, are located at the transparent plate (4) and equally spaced between the indicators (8A and 8B). As described above, the scale (14) is printed on or is embedded in the transparent plate (4), in the form of a ruler for instance, to provide a length dimension. The scale (14) is used to determine the actual size of an overjet as illustrated in FIG. 5. As seen in FIGS. 2 and 4, the linear scale (14) is shown for the purpose of being legible to the reader of this disclosure. In the actual embodiment for use with a patient, the scale (14) is printed on the transparent plate (4) in a reverse image such as shown in FIG. 7. In doing so, the linear scale (14), when reflected in the mirror, is reversed. The reversed image is reflected in a correct orientation for a camera (18) for taking the photograph of the linear scale (14) reflected to the mirror (2).

As seen in FIG. 5, the size of the overjet or a Class III relation is determined using the transparent plate (4) and a distance between a lower centrally located incisor (15) located at stop (10), and the upper incisor (16). The stop (10), also seen in FIG. 4, extends from a back side of the mirrored plate (2) and is located on the mirrored plate (2) to determine a range of generally known overjets or Class III amounts with respect to the transparent plate (4). In FIG. 7, the linear scale (14) is shown as a reverse image for the reader. The stop (10) is moved into contact with an outside surface of the lower incisor (15) and the mouth is closed sufficiently such that an upper most labial incisor (16) contacts the transparent plate (4). The distance between the lower incisor (15) and the upper incisor (16) is measured with the scale (14) using the numbers. Because the plate (4) is transparent, the location at which the upper incisor (16) contact the plate is determined by which number is seen at the incisor contact point. The scale (14) includes a stop line (9) to indicate the location of the stop (10) when the device (1) is closed and the plate (2) and plate (4) are generally parallel. The line (9) also is used, if desired, to determine the overjet by an alternative distance from the stop (9) forward along the scale (14) to the dimensional indicator (8A).

Figure 6:
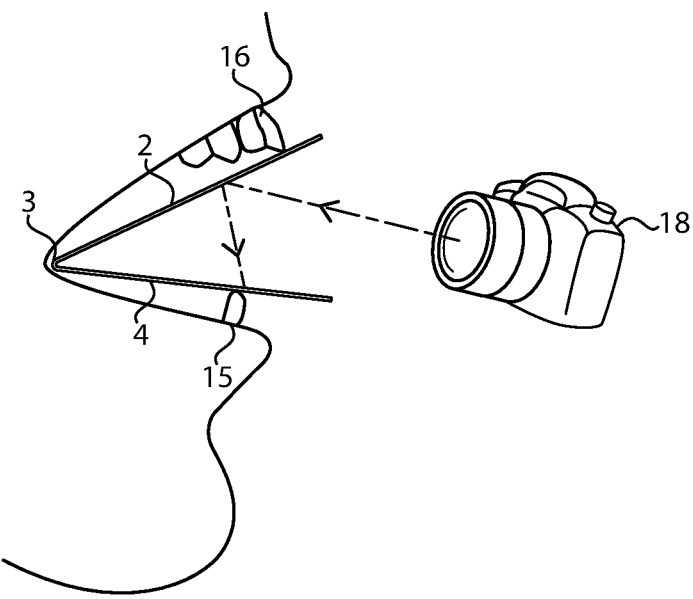
FIG. 6 illustrates a side view of a photo enhancer device in an open position located in an individual's mouth to show how the lower arch is viewed.

Further measures are made with the mouth open, as illustrated in FIG. 6, with a camera (18) focused onto the mirror plate (2) which reflects to the lower incisors (15) seen through the transparent plate (4). This view provides a relatively accurate image of the anterior teeth, the available and required spaces, sizes of appliances, and any other information determined from the anterior arch. The anterior indicator (8A) and posterior indictor (8B) are used to determine the enlarged or reduction of the image of the dentition to obtain greater accuracy of the measures.

Figure 3:
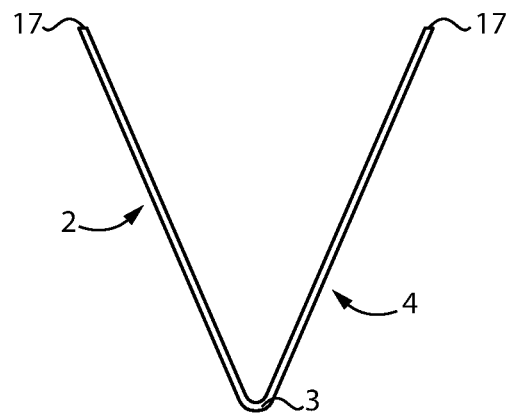
FIG. 3 illustrates a side view of a photo enhancer device.

As illustrated in FIGS. 3 and 5, the two plates, mirror plate (2) and transparent plate (4) are of minimal thickness (17) and are connected by the living hinge (3) as shown in FIGS. 1, 2, 3, 5 and 6. In one or more embodiments, the thickness of the two plates, when one is placed in planar contact with the other, includes a range of thickness from substantially 2 mm to substantially 7 mm.

The stop (10) is located on the underside of the mirrored plate (2), to be able to position the photo enhancer device (1) to contact the most labial lower central incisor (15). This stop is used as an initial point of measurement of the upper most labial incisor (16) when the photo enhancer device (1) is completely closed and is placed over the lower dentition as seen in FIG. 5. The transparent plate (4) faces upwardly and then the distance from the lower incisal stop (10) to the most labial upper central incisor (16) position is measured on the scale (14) indicating the severity of the overjet. The actual location of the stop (10) that extends from the plate (2) is determined based on a known range of over jets that occur generally in a population of users that are intended to use the device (1). For instance, since different sizes of device (1) are considered, the location of the stop (10) is the same for different sizes of devices (1). In this way, the placement of the overjet (10) on the plate (2) accommodates different sizes of individuals using the device (1).

The horizontal line (9) at the transparent plate (4) indicates the same position of the stop (10) that is molded to the opposite side (11) of the mirrored plate (2) to indicate the initial position from which the measurement is taken to the furthest incisor (16) of the upper arch to indicate the severity of the overjet.

The measures (14) located on the transparent plate (4) appear in increments forwardly located from the position of the line (9) and the stop (10) in order to measure the over jet once the photo enhancer (1) is placed over the lower arch in the closed position (FIG. 5) with the transparent plate (4) facing upward from the lower arch. These measures, in different embodiments, are in the form of numbers or letters or whatever to enable a person or a computer software program to actually measure or to verify a computer measurement of the overjet, the distance from the line (9) and stop (10) against the lower incisors (15) to the incisal edge of an upper incisor (16) indicating the overjet amount. Because the locations of the line/stop are known and the scale marking are known, the computer program reads the photograph and provides the measurements of overjet, tooth sizes, and tooth spacing.

The computer program, in one embodiment, resides on a computing device, such as a computer laptop, a computer desktop, workstations, notebook computers, or other computing devices including cellular devices and smartphone. In one or more of these devices, the computer software is resident on the device itself or is resident in the "cloud" and accessed using the computer through a web-based application.

In one embodiment of using the photo enhancer device, an initial photo is usually taken of the lower arch, since it is somewhat easier or more straightforward than photographing the upper arch first. The photo enhancer device (1) is placed in the mouth with the transparent plate (4) positioned in direct contact with the lower dentition (FIG. 6). The patient then opens their mouth as wide as possible, while the upper mirrored plate (2) opens up automatically without the need for an externally applied force. The camera (18) is focused against the mirrored plate (2) which is located at the upper dentition and which is positioned to take a photograph of the entire lower arch. While the photographer adjusts the camera for imaging the dentition, the patient is asked to hold the transparent plate against the entire lower arch with handles (5) and (6) in contact directly with both the anterior and posterior teeth of the lower arch. Once taken, the resulting photograph provides an image showing the occlusal and incisal surfaces of the patient's lower arch. The photograph consequently provides a quite accurate photo that includes not only the photographed surfaces of the lower arch but also includes the measurement indicia (8A), (8B), (9), and (14). As seen in FIG. 2, the measurement indicia (8A), (8B), (9), and (14) is centrally located within the lower arch and consequently does not obstruct the dentition which is being photographed.

Once the photograph of the lower arch is taken, the next photograph is taken of the upper arch. To take this photograph, the transparent plate (4) is held directly against the upper arch in the substantially the same way to completely and directly contact the entire upper arch. The patient opens their mouth as wide as possible while holding this transparent plate (4) against the upper arch in direct contact with the upper arch using the handles (5) and (6). The photograph is then taken by aiming the camera at the mirrored plate (2), now located at the lower arch, to take the photograph of the entire upper arch.

The next photograph is taken with the photo enhancer device (1) in a closed position (See FIG. 5). The device (1) moved along the lower dentition in a rearward direction toward the molars until the stop (10) touches the most labially-positioned lower central incisor (15). The patient then closes his or her mouth until the upper central incisors (16) contact the transparent plate (4). A photograph is then taken of the transparent plate (4), which is located above the mirrored plate (2) by aiming the camera generally perpendicular to the surface of the plate (4). Generally, the camera is aimed toward the plate in a direction that is as close to a right angle with respect to the plate (4) as possible. Either the patient or person taking the photograph can hold the upper lip away from plate which helps to reveal the line (9) indicating the upper incisors (16) position on the scale (14) where the upper incisor contacts the plate (4). In another embodiment, the photograph is taken with cheek retractors in place to hold the upper lip up and out of the way without the help of anyone else.

FIG. 7 illustrates a front view of an intraoral hinged mirrored photo device 1 including the transparent plate 4 having measurement indicia (8A), (8B), (9), and (14) and the mirrored plate 2. The device 1 is shown in an open position in which the hinge 3 has opened the device 1 such that the mirrored plate 2 and the transparent plate 4 are separated. In one embodiment, the hinge 3 has a sufficient resiliency such that an angle between the mirrored plate 2 and the transparent plate 4 is less than ninety (90) degrees in the absence of any external forces when place on a level surface. In this way, when the device 1 is placed in a patient's mouth, manipulation of the device 1 is reduced for placement. Other angles of between the mirrored plate 2 and the transparent plate 4 are contemplated. The hinge 3 includes a sufficient resiliency to maintain the living hinge in an open position in the absence of an externally applied pressure.

Figure 8A:
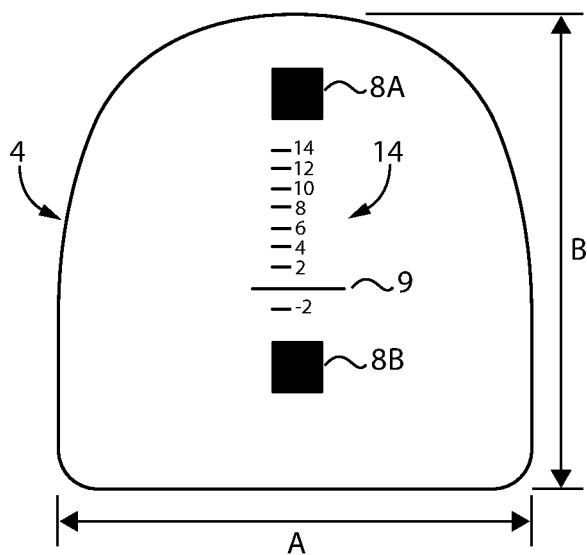
FIGS. 8A and 8B illustrate embodiments of two different sizes of the transparent plate.
Figure 8B:
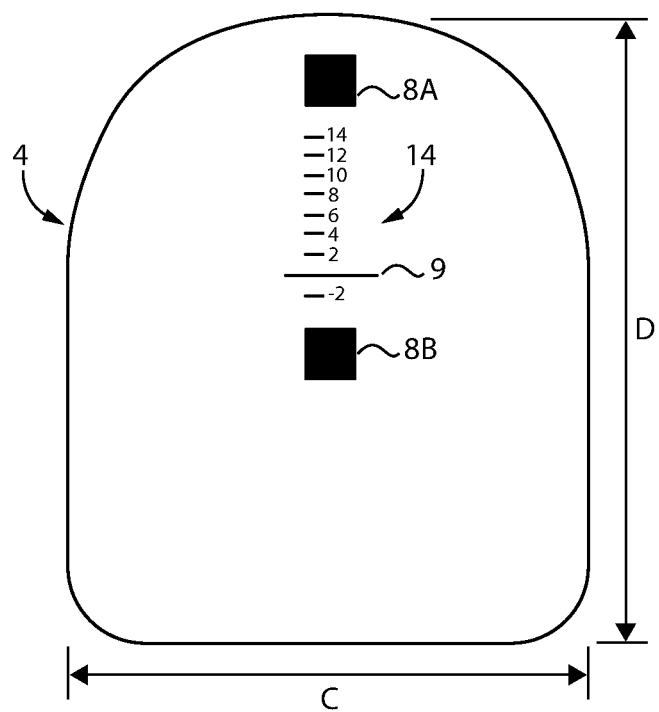

There is contemplated two different sizes of the transparent plate 4 as illustrated in FIGS. 8A and 8B. The mirrored plate 2 of a smaller version of FIG. 8A typically includes the same dimensions as the transparent plate 4. In the smaller version, the transparent plate 4 includes a width A of about 1.9 inches (1¹¹⁄₁₆ inches, 48.3 mm) and a length B of about 1.9 inches (1¹⁵⁄₁₆ inches, 48.3 mm). Using this size of the transparent plate 4 provides a device 1 that is to be used by children who generally have oral cavities smaller than young adults and adults. The linear scales (14) in both FIGS. 8A and 8B are of the smaller size in the smaller version of FIG. 8A also occur in a reverse image to be legible for the reader. In an actual embodiment, the scales are printed in a reverse image such as illustrated in FIG. 7.

The transparent plate 4 of the larger size, as seen in FIG. 8B, includes a width C of about 2.1 inches (2¹⁄₁₆ inches, 52.5 mm) and a length of about 2.49 inches (2½ inches, 63.35 mm). Consequently, a patient using a device 1 having this size of transparent plate 4 would generally be a young adult or adult.

Since different sizes are required for different ages of patients, two or more devices 1 are provided as a kit in some embodiments. A set of orthodontic tools, the devices 1, are used to diagnose an orthodontic problem of two or more patients or a single patient as the patient ages. The kit includes at least a first size of device 1 and a second size of device 1, each of which accommodates different sizes of oral cavities of one or more patients. The different sized devices 1 would be placed in a single package for delivery as a single group of devices. In other embodiments, there are more than two different sized devices.

The mirrored photo enhancer springs open with the mirror surface facing downward up against the upper arch when the mouth is sufficiently wide open. The printed information (as shown in FIGS. 2 and 4) is printed on a transparent see-through plastic. This see-through element is positioned against the lower arch with the hinge connecting both plates being positioned in the rear of the open mouth. This is the process for taking a picture of the lower arch. The person taking the photo aims the cell phone or camera toward the upper mirrored plate and takes a picture of the lower dentition.

To take a photo of the upper dentition, the process is reversed. The mirrored plate is positioned against the lower dentition with the mirror facing upward. The printed plate (as in FIGS. 8A and 8B) is placed against the upper arch and again with the hinge located toward the back of the mouth. The small handles, i.e. element numbers 5, 6, 12, and 13 of FIG. 4 are used by the patient to hold the transparent plate against the tops (incisal and occlusal surfaces) of the teeth in order to position the see-through plate with the printing directly against the teeth. The above two procedures produce an upper and lower image directly showing the tops of all the lower and upper teeth.

In one or more embodiments, a plain white partial, sectional, or full sized removable magnetic white cover 20, is located between the mirrored plate and the transparent plate to eliminate a reflection from the mirrored plate. See FIG. 5. The white plate prevents a reflected image of the printed transparent plate from appearing as a double image when the photograph is taken in order to measure the over jet. This white plate can be secured by magnetism to a metal mirrored plate using an appropriate magnetic metal, so that it remains in place when photographs are being taken for the measurement of over jet. This prevents inaccurate measures taken by the computer. In other embodiments, the plate that is inserted between the mirrored plate and the transparent plate is not white but is of another color to provide sufficient contrast to see the measurement indicia on the transparent plate. By using the plate, the double images are eliminated. If not eliminated, the computer has a difficult time interpreting the double images which produce inaccurate measurement of overjet. In actual use, the plates 4, the magnetic removable white cover 20, and 2 are in contact with one another.

The next photo is taken with a fold up device in a closed position so that the mirrored plate is directly in close contact with the transparent plate as shown in FIG. 5. The device is pushed rearward in the mouth until the stop 10 is engaged against the lower front teeth or tooth 15. The patient is then asked to close their teeth while the stop 10 remains against the lower front tooth 15 and the cell phone or camera is held vertically so that a picture is taken of the upper front tooth 16 against the printing with the small horizontal lines 14 indicating the amount of overjet or Class III present for the patient's dentition. Once the photos have been taken, the computing device, using the computer software, analyzes each of the three photos to determine the occlusal and incisal edges of the teeth as well as the distance from the lower front teeth (central incisors) or tooth to the upper front tooth which indicates the overjet. Also, from the lower (and upper) occlusal views, the available and required spaces are measured to determine the width of the front teeth and the size of the appliance which is to be used for a particular individual's case. Using this information, the practitioner determines the status of the teeth and arches and determines a course of action to address any issues or faults with the teeth and/or arches. In some embodiments, the computer software is configured to provide treatment recommendations, severity of the crowding, spacing, overjet, Class III conditions as well as the size and type of appliance to be used and also a suggested course of action which the practitioner reviews and determines, based on the suggestions, a course of action to address any identified deficiencies.

While exemplary embodiments incorporating the principles of the present disclosure have been described herein, the present disclosure is not limited to such embodiments. Instead, this application is intended to cover any variations, uses, or adaptations of the disclosure using its general principles. Further, this application is intended to cover such departures from the present disclosure as come within known or customary practice in the art to which this disclosure pertains.

What is claimed is:

1. A photo enhancer device for imaging dentition of an individual comprising:
   a transparent plate;
   a mirrored plate connected to the transparent plate with a living hinge to form a one piece unitary part, wherein the transparent plate and the mirrored plate are sized to fit, at least partially, in the mouth of a patient for imaging the individual's dentition; and
   a measurement indicia positioned on the transparent plate at a location at which the measurement indicia is reflected by the mirrored plate, the measurement indicia provides dimensional information for at least an arch of the individual that is visible through the transparent plate.

2. The photo enhancer device of claim 1 wherein the transparent plate and the mirrored plate are sized to provide occlusal images of the lower and upper arches.

3. The photo enhancer device of claim 2 wherein the living hinge includes a stiff and strong living hinge having a sufficient resiliency to maintain the living hinge in an open position in the absence of an externally applied pressure.

4. The photo enhancer of claim 2 wherein the measurement indicia is configured to provide one or more of the following: 1) size determination of the upper and lower teeth, 2) available spaces between teeth; 3) required spaces between teeth; 4) crowding and spacing of teeth; 5) broken contacts; 6) sizes of various dental appliances, 7) arch widths; 8) severity of an over jet; 9) severity of a Class III mandibular overgrowth; 10) and other measurements required for a diagnosis of an orthodontic problem.

5. The photo enhancer device of claim 1, wherein the measurement indicia includes a first two-dimensional indicator spaced from a second two-dimensional indicator, wherein each of the first and second two-dimensional indicators are printed or embedded in the transparent plate and have first and second sides of a known length, wherein a photograph of the dentition and of the first and second two-dimensional indicators enables determining sizes of the photographed dentition.

6. The photo enhancer device of claim 5 wherein the transparent plate includes a centerline along which the first and second two-dimensional indicators are located, the centerline being positioned relative to the mirrored plate for reflection of the centerline by the mirrored plate.

7. The photo enhancer device of claim 6 wherein the measurement indicia includes a measurement scale located along the centerline between the first and second two-dimensional indicators to determine distances of the photographed dentition.

8. The photo enhancer device of claim 7 wherein the measurement indicia includes a stop line, wherein the stop line indicates a position of the transparent plate with respect to a lower incisor of the patient.

9. A photo enhancer device for imaging dentition of an individual comprising:
   a transparent plate;
   a mirrored plate connected to the transparent plate with a living hinge to form a one piece unitary part, wherein the transparent plate and the mirrored plate are sized to fit, at least partially, in the mouth of a patient for imaging the individual's dentition,
   wherein the mirrored plate includes a mirror located on one side of the plate and a stop extending from another side of the plate, wherein the stop is adapted to engage a lower incisor to measure an overjet with an upper central incisor.

10. The photo enhancer device of claim 9 further comprising measurement indicia located at the transparent plate, wherein the measurement indicia provides dimensional information for the upper and lower arches.

11. The photo enhancer device of claim 10 wherein the measurement indicia includes a first two-dimensional indicator spaced from a second two-dimensional indicator, wherein each of the first and second two-dimensional indicators have first and second sides of a known length, wherein a photograph of the dentition and of the first and second two-dimensional indicators enables determining sizes of the photographed dentition.

12. The photo enhancer device of claim 11 wherein the transparent plate includes a centerline along which the first and second two-dimensional indicators are located.

13. The photo enhancer device of claim 12 wherein the measurement indicia includes a measurement scale located along the centerline between the first and second two-dimensional indicators to determine distances of the photographed dentition.

14. The photo enhancer device of claim 13 wherein the measurement indicia includes a stop line, wherein the stop line indicates a position of the stop when the mirrored plate and the transparent plate are in a closed position.

15. The photo enhancer device of claim 14 wherein the mirrored plate or the transparent plate includes one or more handles to enable the mirrored plate or the transparent plate to be held in contact with the dentition of either the lower arch or the upper arch.

16. A photo enhancer device having a mirrored plate and a transparent plate used to diagnose an orthodontic problem of a patient, the photo enhancer device comprising:
   a living hinge connecting the mirrored plate with the transparent plate, wherein the living hinge opens forcibly automatically as the patient opens their mouth and substantially prevents the patient from breathing directly on the mirror which eliminates a problem of clouding up the mirror which interferes with the clarity of photographs utilizing the photo enhancer device; and
   a white plate that inserts over the mirrored plate and is held in place by magnetism to substantially prevent a double image of measurement indicia located on the transparent plate when the mirrored plate and transparent plate are held together in order to measure over jet.

17. The photo enhancer device of claim 16, wherein the living hinge comprises a strong and stiff living hinge fixedly connected to the mirrored plate and the transparent plate to provide a unitary photo enhancer device.

18. The photo enhancer device of claim 17 wherein the living hinge comprises polypropylene or other plastic having a sufficient resiliency to open by itself in the absence of an externally applied pressure.

19. A set of orthodontic tools used to diagnose an orthodontic problem of one or more patients, the set comprising:
- a first photo enhancer device including a first transparent plate connected to a first mirrored plate with a first living hinge, wherein the first photo enhancer device includes a first size;
- a second photo enhancer device including a second transparent plate connected to a second mirrored plate with a second living hinge, wherein the second photo enhancer device includes a second size; and
- wherein the first size and second size are different sizes adapted to accommodate different sizes of oral cavities of the one or more patients, and
- wherein, the first photo enhancer includes a handle that extends away from at least one of the mirrored plate and the transparent plate at a front end of the first photo enhancer device, the first living hinge being positioned at an end of the photo enhancer device that is opposite of the front end.

20. The set of orthodontic tools of claim 19, wherein the different sizes are adapted to accommodate different sizes of teeth and the number of teeth present at various ages from an infant through adulthood of the one or more patients.

21. The claim 19, wherein the handle comprises a first handle of the first mirrored plate and a second handle of the first transparent plate.

22. The set of orthodontic tools of claim 19, wherein the first handle comprises a first pair of lateral handles, each lateral handle of the first part of lateral handles being inclined relative to a centerline of the first photo enhancer device.

23. A method of imaging dentition of an individual comprising:
- providing a photo enhancer device used to diagnose an orthodontic problem of a patient, the photo enhancer device having a mirrored plate and a transparent plate connected with a living hinge;
- imaging, at a first time, the dentition of the individual using the photo enhancer device to arrive at an initial diagnosis of the individual, wherein imaging, at the first time, includes capturing a measurement indicia positioned on the transparent plate with a first image of at least a portion of an arch of the patient from a first reflection provided by the mirrored plate;
- imaging, at a second time, the dentition of the individual using the photo enhancer device to arrive at a follow-up diagnosis of the individual to determine a progress of treatment for a malocclusion, wherein imaging, at the second time, includes capturing the measurement indicia positioned on the transparent plate with a second image of at least a portion of the arch of the patient from a second reflection provided by the mirrored plate.

24. The method of claim 23 further comprising:
- imaging, at one or more times after the second time, the dentition of the individual using the photo enhancer device to arrive at additional follow-up diagnoses of the individual to determine the progress of treatment for the malocclusion.

25. A photo enhancer device for imaging dentition of an individual comprising:
- a transparent plate;
- a mirrored plate connected to the transparent plate with a living hinge to form a one piece unitary part, wherein the transparent plate and the mirrored plate are sized to fit, at least partially, in the mouth of a patient for imaging the individual's dentition;
- a measurement indicia located at the transparent plate, wherein the measurement indicia provides dimensional information for the upper and lower arches, wherein the measurement indicia comprises a QR code.

* * * * *